United States Patent [19]

Joa

[11] 4,284,454
[45] Aug. 18, 1981

[54] METHOD AND APPARATUS FOR APPLYING ELASTIC BANDS TRANSVERSELY TO A DIAPER LINE

[76] Inventor: Curt G. Joa, P.O. Box 1121, Boynton Beach, Fla. 33435

[21] Appl. No.: 147,996

[22] Filed: May 12, 1980

[51] Int. Cl.³ .............................................. B32B 31/10
[52] U.S. Cl. .................................... 156/163; 156/229; 156/265; 156/303; 156/494; 156/519; 156/552; 156/560
[58] Field of Search ............... 156/160, 161, 163, 164, 156/250, 256, 265, 494, 495, 519, 552, 559, 560, 303, 229; 112/127.27, 262.1

[56] References Cited

U.S. PATENT DOCUMENTS

| 2,976,199 | 3/1961 | Rand ..................................... 156/163 |
| 3,560,292 | 2/1971 | Butter .................................... 156/160 |
| 3,644,157 | 2/1972 | Draper .................................... 156/160 |
| 3,819,401 | 6/1974 | Massengale et al. ................. 156/229 |
| 3,981,763 | 9/1976 | Brocklehurst ........................ 156/519 |
| 4,081,301 | 3/1978 | Buell ..................................... 156/229 |
| 4,227,952 | 10/1980 | Sabee .................................... 156/164 |

Primary Examiner—Jerome W. Massie
Attorney, Agent, or Firm—Wheeler, House, Fuller & Hohenfeldt

[57] ABSTRACT

Method and apparatus for attaching elastic bands to a web comprised of absorbent articles such as diapers which are fabricated to lie transversely of the length of a continuous fabrication line. The bands are stretched in a direction transverse to the fabrication line and are attached to the web in their stretched condition and are maintained in stretched condition transversely to the web until the article is fabricated.

12 Claims, 17 Drawing Figures

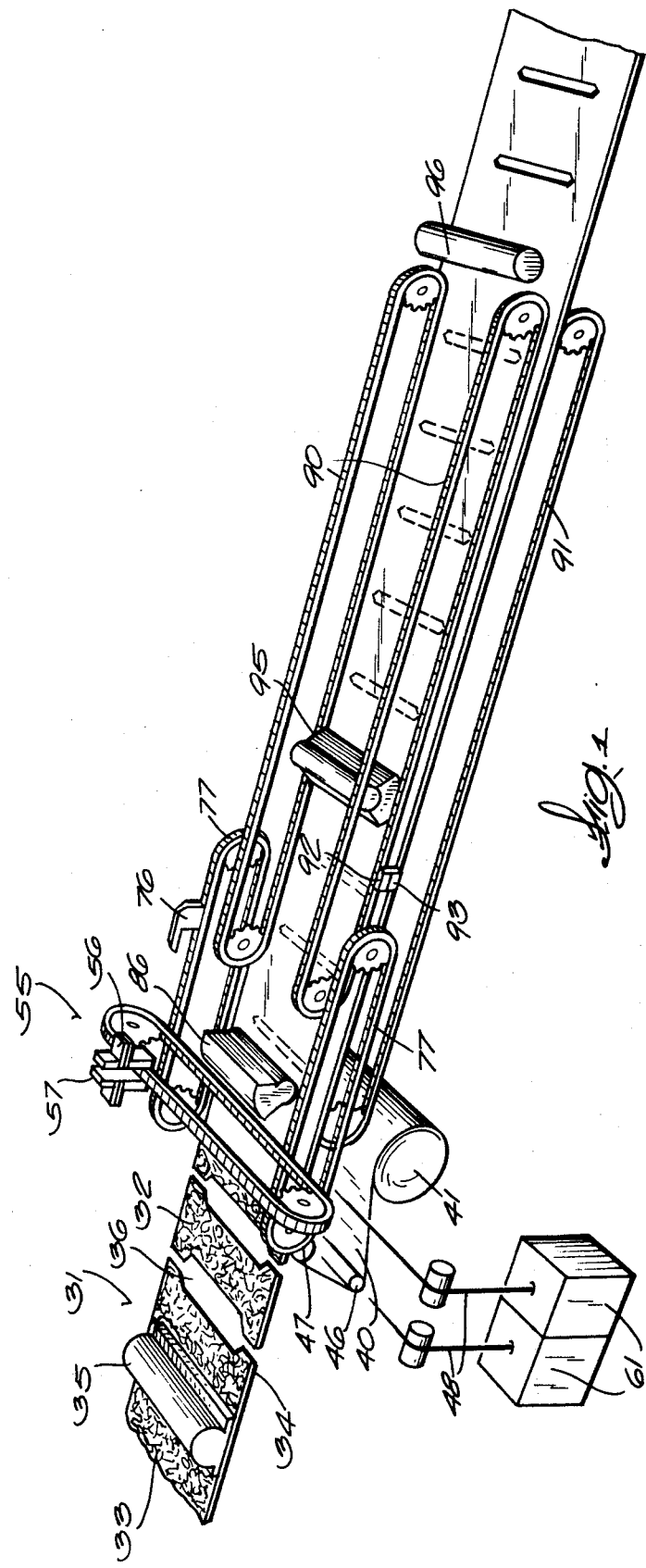

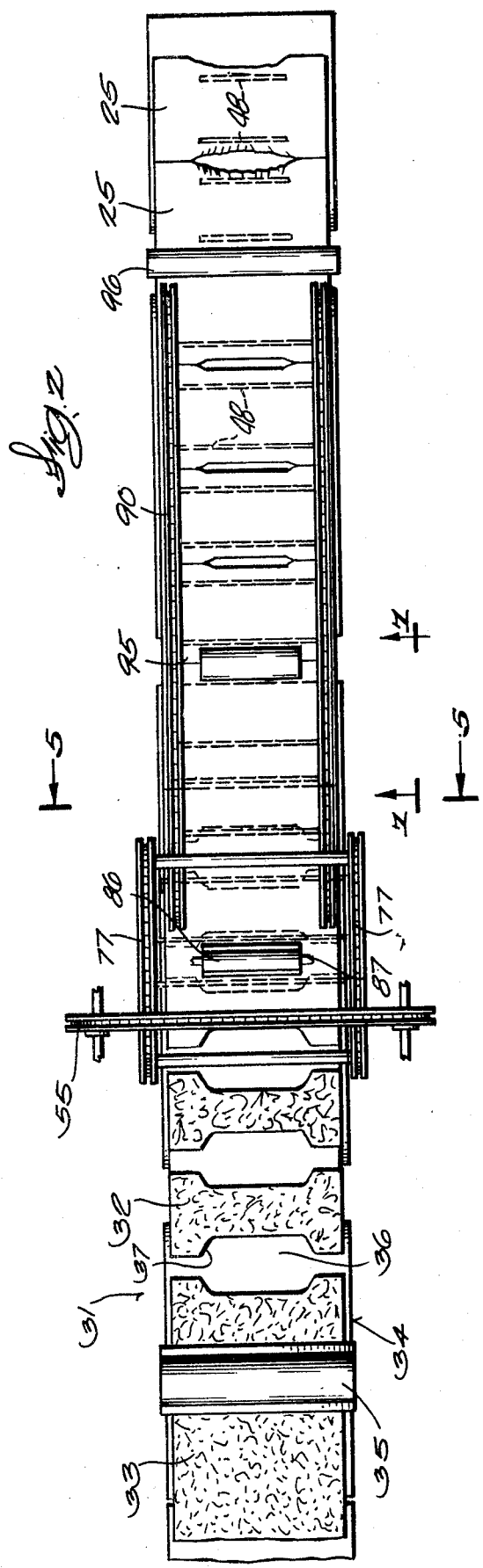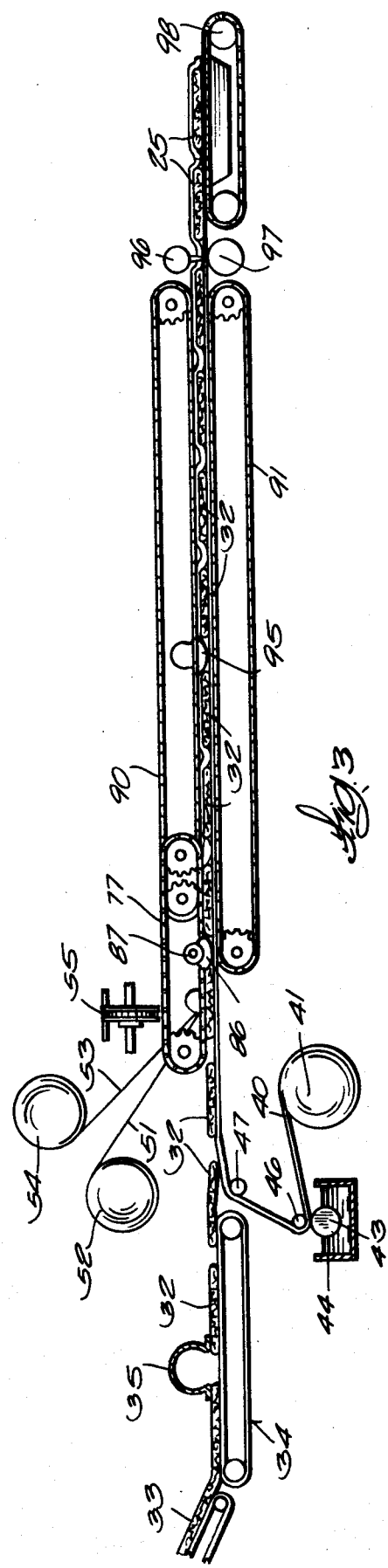

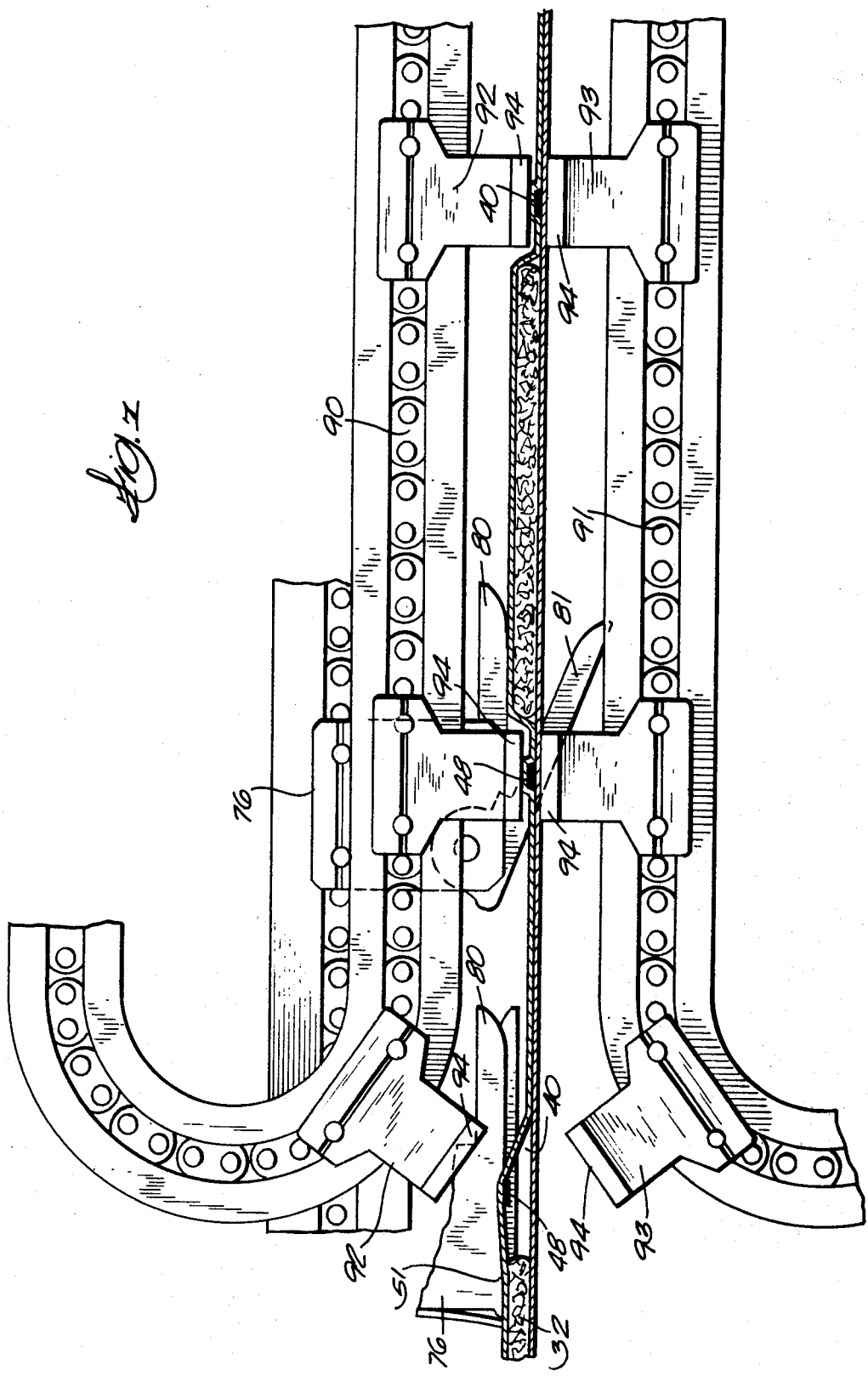

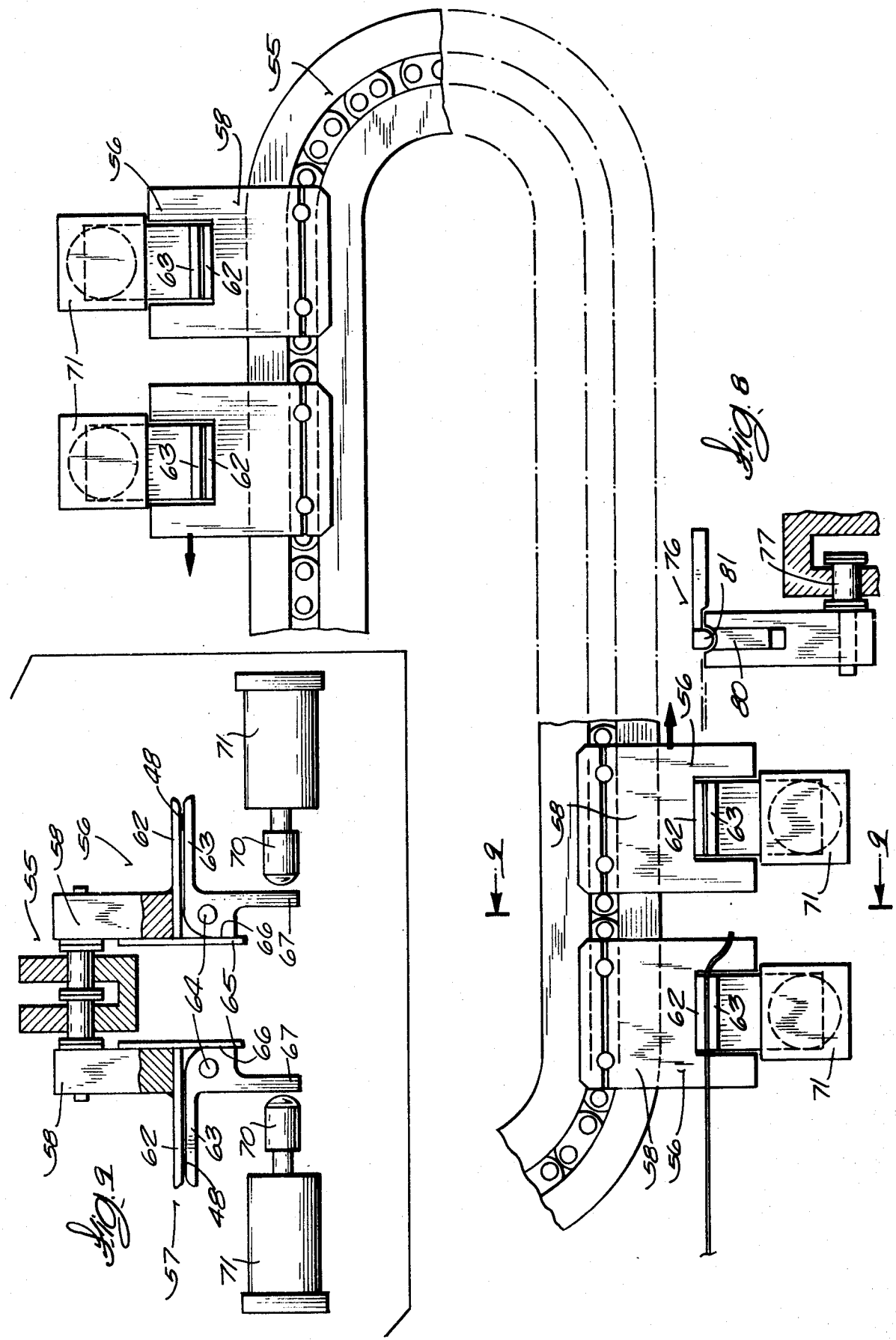

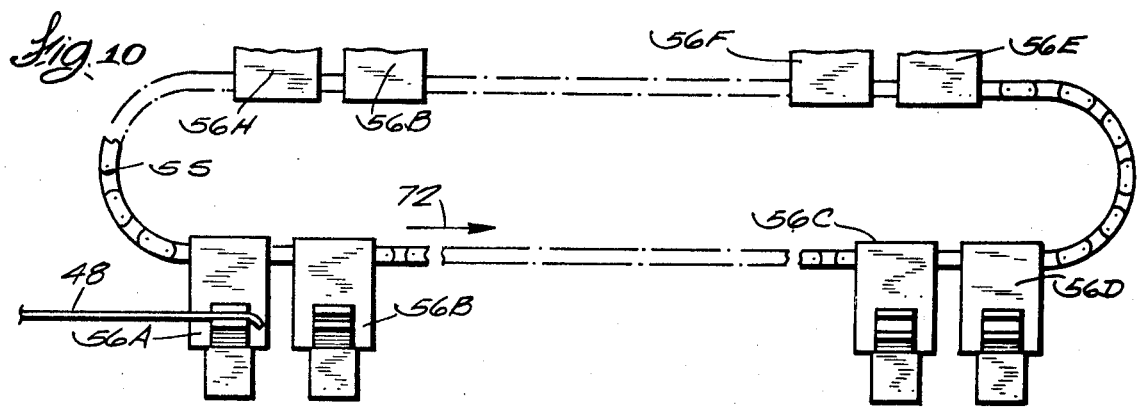
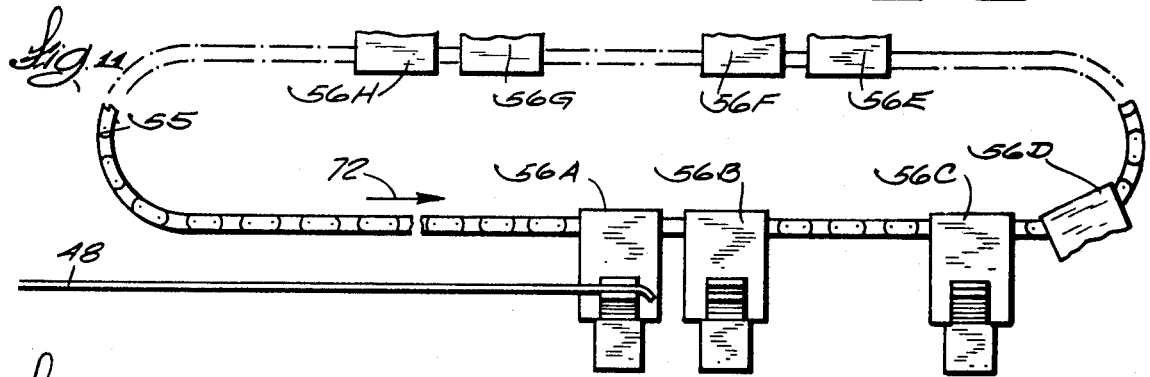
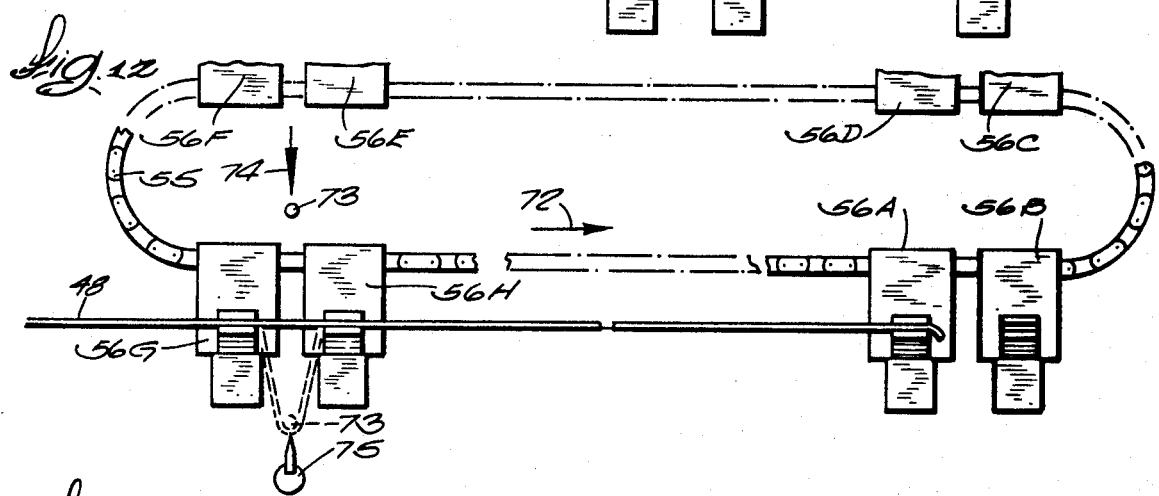
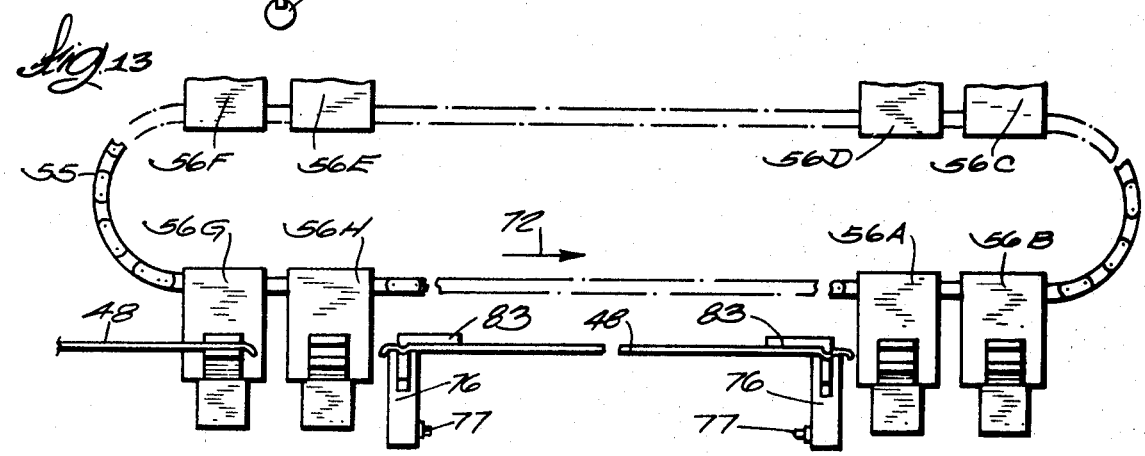

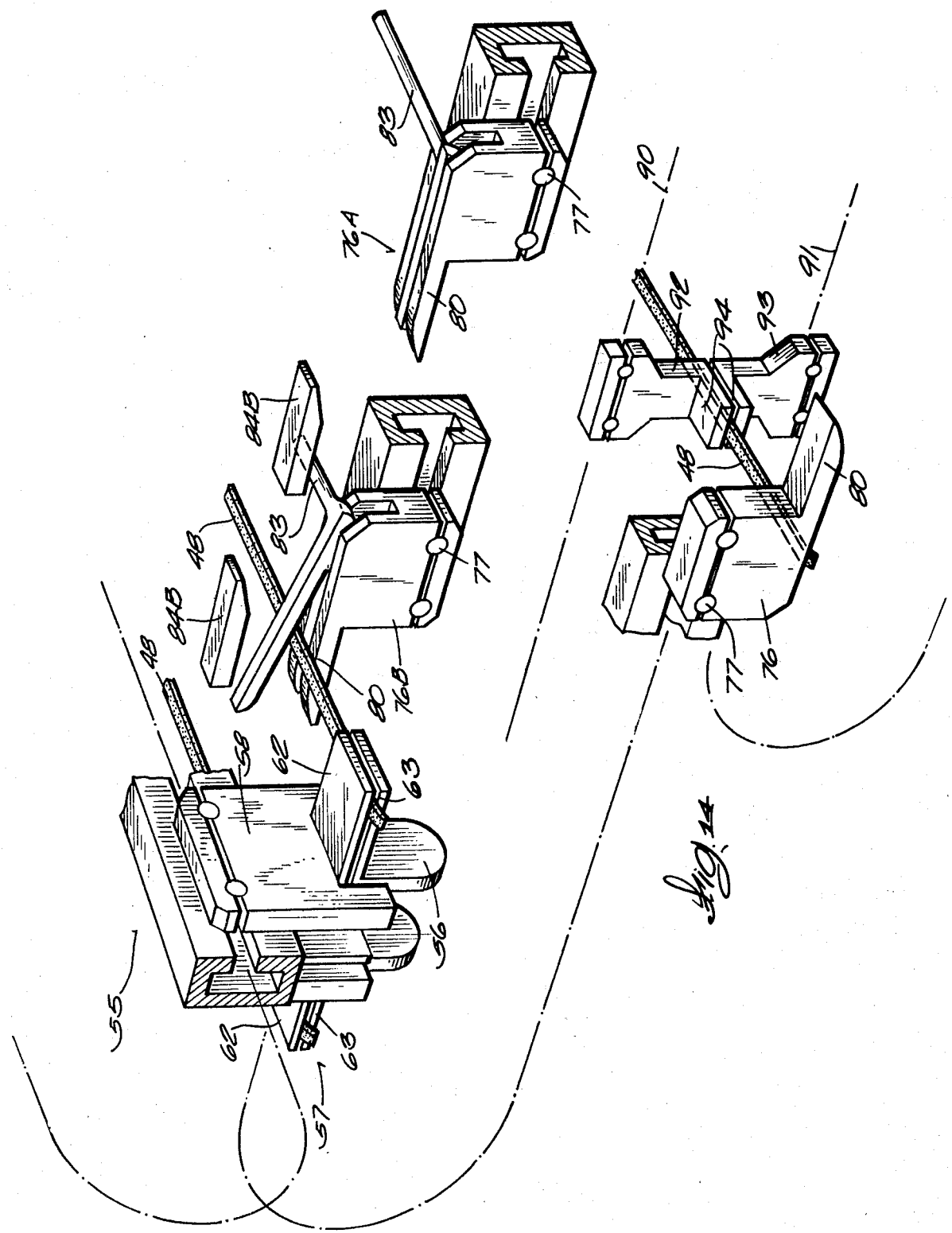

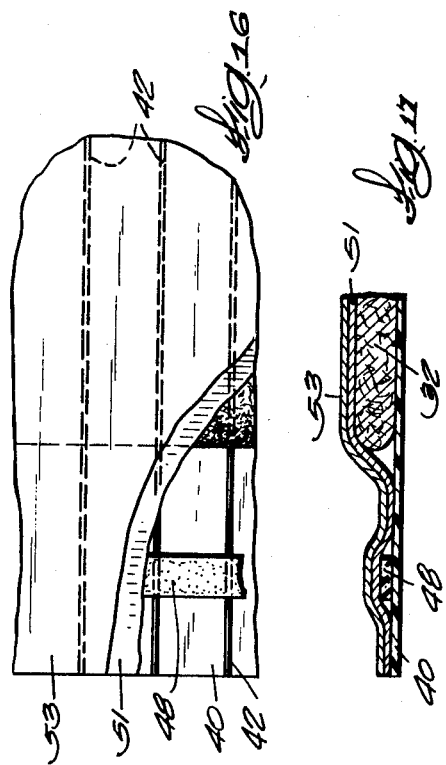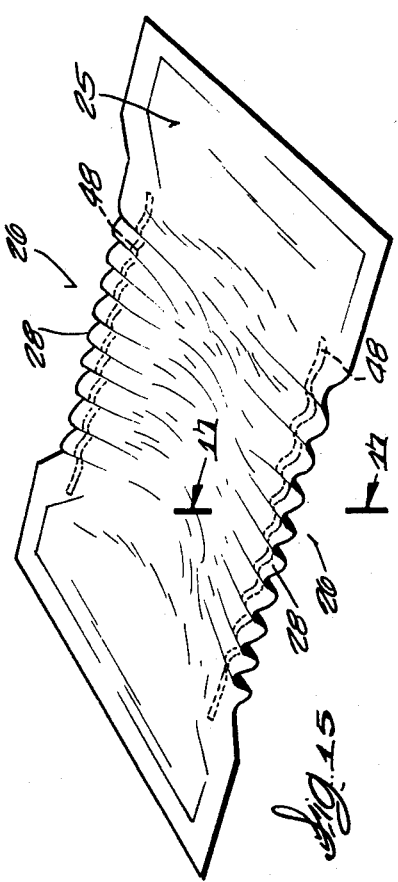

METHOD AND APPARATUS FOR APPLYING ELASTIC BANDS TRANSVERSELY TO A DIAPER LINE

U.S. Pat. No. 4,081,301 shows method and apparatus for a web or continuous sequence of disposable diapers in which the absorbent pads comprising each diaper are arranged end-to-end longitudinally of the fabrication line and pre-stretched elastic bands are fed in the longitudinal direction for being applied and adhered to a backing sheet on which the pads are supported.

The present invention takes a different approach in that the pads are formed so their lengths are disposed transversely of the longitudinal direction in which the pads are transported and the elastic bands are fed in stretched condition crosswise or transversely of the longitudinal direction and are adhered to the pads while in said transverse position.

SUMMARY OF THE INVENTION

To apply stretched elastic bands to the continuous web transversely of the direction in which the diapers are moving, the bands are indexed into a position above and crosswise of the pads and moving backing sheet. In the course of indexing the bands into such transverse position, the bands are stretched, cut to length, and are then transferred into contact with glue areas previously applied to the pads. The cut lengths of bands are maintained in stretched condition transversely to the web until the glue sets to hold the bands to the pad, whereupon the bands are allowed to contract to pleat the pad.

In the illustrated embodiment two such bands for one diaper are simultaneously stretched transversely of the fabrication line. The bands are spaced apart in the longitudinal direction of the fabrication line by a distance equal to the desired spacing between the bands in a single diaper.

Other objects, features and advantages of the invention will appear from the disclosure hereof.

DESCRIPTION OF THE DRAWINGS

FIG. 1 is a diagrammatic perspective view of apparatus to carry out the invention;

FIG. 2 is a plan view of the apparatus shown in FIG. 1;

FIG. 3 is a side view of the apparatus shown in FIG. 1;

FIG. 7 is an enlarged fragmentary view taken along the line 7—7 of FIG. 2;

FIG. 8 is a view showing details of the band-stretching apparatus;

FIG. 9 is a fragmentary cross section taken along the line 9—9 of FIG. 8;

FIGS. 10, 11, 12 and 13 are successive diagrammatic views showing steps in stretching the elastic bands;

FIG. 14 is a fragmentary perspective diagrammatic view showing the transfer of bands from the transverse band stretcher to the pads;

FIG. 15 is a diagrammatic view of a diaper pad with transverse elastic bands fixed thereto and released so as to pleat the pad;

FIG. 16 is a fragmentary diagrammatic view showing a portion of an elastic band in stretched condition as applied to the glue stripes on a pad;

FIG. 17 is a cross section taken along the line 17—17 of FIG. 15.

DESCRIPTION OF A PREFERRED EMBODIMENT

Figure 5:
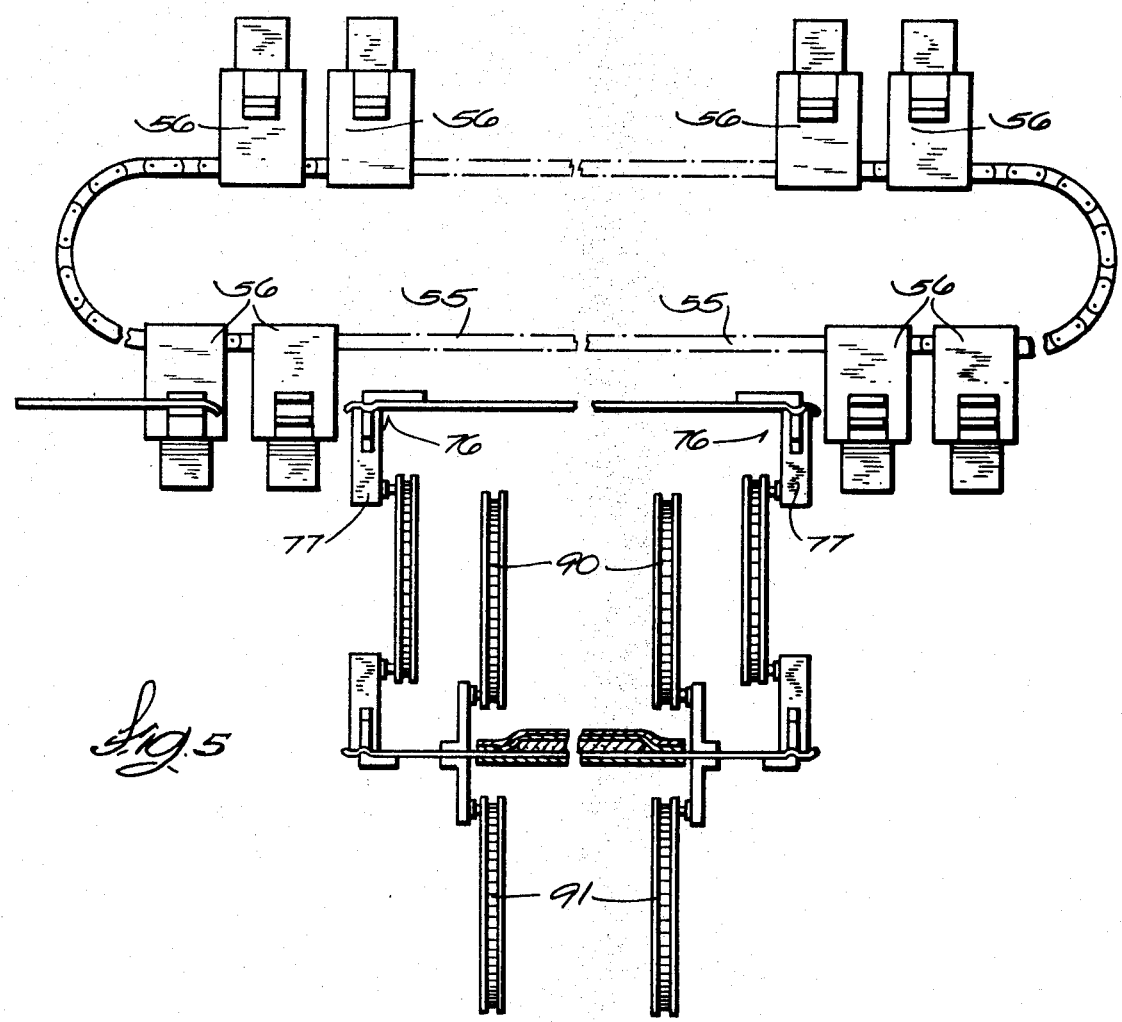
FIG. 5 is a cross section taken along the line 5—5 of FIG. 2.

A disposable baby diaper 25 made according to the present invention is shown in FIG. 15. The diaper 25 typically has its sides cut out in the crotch region 26 to faciliate contouring it to a baby. Elastic bands 48 are glued while they are in a stretched condition and while the diaper is completely flat in the production line so that after the glue sets and the bands are released and allowed to contract, they will pull the side edges of the diaper into pleats 28 along its mid-portion. When the diaper is applied to the baby, the pleats are pulled out somewhat by the stretching of the elastic bands 48, thus maintaining good closing pressure against the baby's thighs to prevent leakage.

The present invention relates to the method and apparatus for attaching elastic bands 48 to successive diapers in a production line 31 as shown in FIGS. 1 and 2 which the respective absorbent filler pads 32 have their lengths transversely or laterally of the longitudinal direction in which the diaper web is transported during fabrication in production line 31.

In this arrangement, a continuous layer of pad filler material 33, such as fluffed paper pulp, is conveyed on a series of belt conveyors such as 34, and a device such as the vacuum hood 35 is utilized to create individual pads 32 by drawing out pad filling material from the continuous layer to produce the spaces 36 between pad fillers 32. The spaces 36 are desirably formed with notches 37 which provide the relieved or offset longitudinal edges 26 of the pad 25 as shown in FIG. 15.

Figure 4:
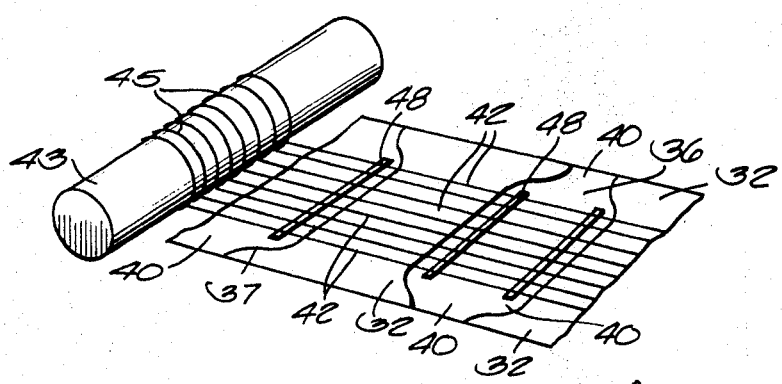
FIG. 4 is a diagrammatic illustration showing how glue lines are applied to the pads.

The absorbent pads 32 are encapsulated with cover material as best shown in FIGS. 2 and 3. A strip of plastic film material 40 such as polyethylene is drawn from a feed roll 41 and is applied beneath the pads 32 after having narrow continuous longitudinally extending glue stripes 42 applied thereto as seen in FIG. 4. The continuous film 40 passes over a glue roller 43, best shown in FIGS. 3 and 4, which is partially immersed in a glue tank 44. The roller 43 has lands or circumferential ridges 45 which project somewhat from the circumference of the roll 43. As the continuous film 40 passes over the guide roller 46, the stripes of glue 42 will be laid onto that side of the film strip 40 which will be uppermost when the film strip passes around guide roller 47 (FIG. 3) to thereby adhere the film strip to the successive individual absorbent pads 32. As best shown in FIG. 4, the glue stripes 42 will be exposed upwardly in the spaces 36 between pads 32. Accordingly, when stretched elastic bands 48 are applied transversely to the film 40 in the spaces 36 and within the notches 37, the bands 48 will adhere to the glue stripes 42, as illustrated in FIG. 4.

As can be seen in FIG. 3, an upper layer of tissue 51 is unreeled from a parent roll 52 and a layer of nonwoven cover material 53 unreeled from a parent roll 54. These layers are deposited on top of the pads 32. Thus, a composite or laminar web, as shown in FIGS. 16 and 17, will be built up. Tissue layer 51 adheres to the glue lines 42 to hold it firmly in place. The composite web is built up while the bands 48 are stretched and maintained in stretched condition to prevent the bands from pleating or wrinkling the diaper until the glue stripes 42 have set to anchor the elastic bands 48.

The elastic bands 48 are stretched and delivered into position laterally or transversely of the longitudinal direction of web movement on the fabrication line 31 by an indexing conveyor 55, details of which are shown in FIGS. 8 and 9 and the operation of which is diagrammatically shown in FIGS. 10–13, inclusive. An indexing chain 55 is provided with fore and aft sets of elastic band grippers 56, 57 (FIG. 9). The reason for the two sets of grippers, a fore set 56 and an aft set 57, is to enable the indexing chain 55 to simultaneously process two elastic bands 48 which are spaced apart longitudinally of the fabrication line 31 a distance equal to their spacing within the space 36 between the notches 37 of the pad fillers 32 (FIG. 4). As hereinafter explained, each set of grippers 56 is made up of four identical grippers positioned along the chain 55, as shown in FIGS. 10, 12 and 13.

The elastic bands 48 are cut from originally continuous elastic ribbons (FIG. 1) that are drawn from supply boxes 61 as shown in FIG. 1 to provide one elastic ribbon for each set of grippers 56, 57. The ribbons are not yet under tension as they are being withdrawn. Tensioning or stretching of the bands is performed by the apparatus shown in FIG. 12.

As is evident in FIG. 9, each set of grippers 56, 57 is mounted on chain 55 by hangers 58. The respective grippers 56, 57 comprise a fixed finger or blade 62, which extends longitudinally of the fabrication line 31, and a movable clamp finger or blade 63 which is mounted to hanger 58 on a pintle 64. Leaf springs 65, also mounted on hangers 58, bear against cam surfaces 66 of the movable blades 63 to normally clamp the clamp fingers 63 against the fixed blade 62 and thereby grip any intervening elastic ribbon 48. The movable fingers 63 are also provided with bellcrank fingers 67 which are subject to the pressure of plungers 70 on fluid motors 71 by which the plungers 70 may be advanced against the bellcrank fingers 67 to open the clamp fingers 63 and release the elastic ribbons 48.

As best shown in the diagrammatic views of FIGS. 10–13, inclusive, there are four sets of each of the clamps 56, 57 on indexing chain 55. Discrete lengths of the two elastic bands 48 are drawn from the containers 61 and are stretched and cut to a predetermined length as illustrated in these figures. The first step is illustrated in FIG. 10, in which the end of one of the unstretched elastic ribbons 48 is engaged between the clamping jaws of the first clamp 56A. Chain 55 then moves to the right in the direction of arrow 72 in FIG. 11, to draw the ribbon 48 toward the right in that view. When first clamp 56A reaches its position in FIG. 12, clamps 56H and 56G, which have their jaws open to accept ribbon 48, have now reached the position shown in FIG. 12 at which point the cylinders 71 are operated in a sequence for the jaws on clamps 56G to become closed while the jaws on clamp 56H are left open. A tension imparting bar 73 is then moved downwardly in the direction of arrow 74 in FIG. 12 to stretch the untensioned ribbon 48 to its stretched length as shown in this figure. When the elastic ribbon is fully stretched, the movable jaw on clamp 56H is closed to establish the stretched length and tension in band 48. After the jaws are closed, a rotating knife 75 cuts the ribbon to isolate a band 48 which has been stretched to a length which will cause the proper amount of pleating in the thigh region edges of the diaper when the band is allowed to relax.

At this point in the cycle two longitudinally spaced stretched elastic bands 48 extend transversely across the diaper fabrication line 31, in readiness to be transferred to the continuous web. See FIGS. 9 and 14. Another set of clamps 76 on continuously moving longitudinally extending transfer chains 77 then take over gripping the stretched bands 48 and the movable jaws on transversely movable clamps 56H and 56A are opened to release the elastic bands 48.

Figure 6:
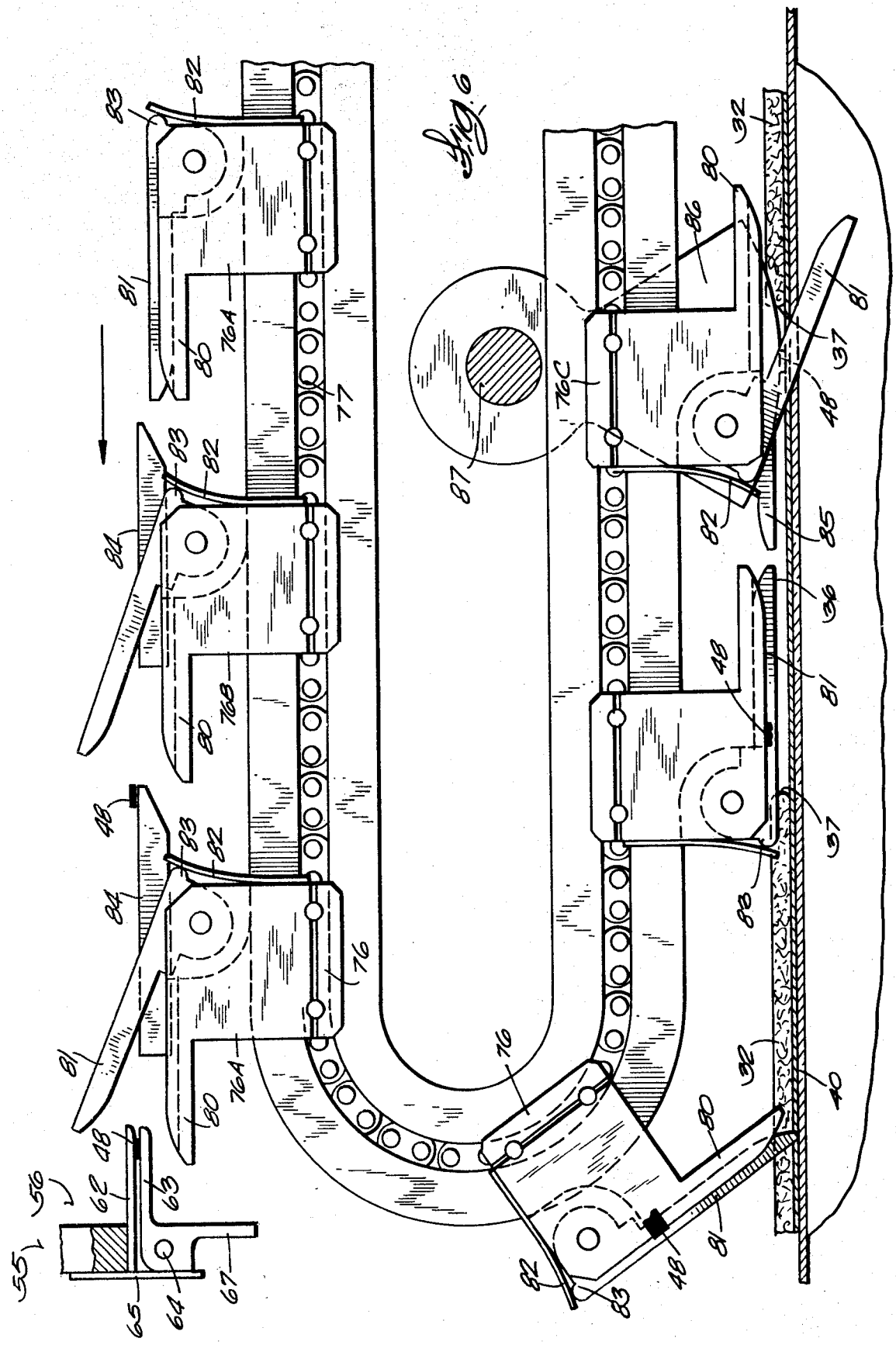
FIG. 6 is an enlarged fragmentary view taken along the line 6—6 of FIG. 2.

As best shown in FIG. 1, the continuously moving transfer conveyor chains 77 are arranged for translating longitudinally of the fabrication line 31. Details of the longitudinally acting chains 77 and their clamps are shown in FIGS. 6 and 14. There are two laterally spaced chains 77 with associated clamps 76, one at each side of the fabrication line 31 and separated by a distance such that the clamps 76 will pick up the stretched and cut bands 48 as shown in FIG. 13. The series of clamps 76 on chains 77 are each substantially identical. As shown in FIGS. 6 and 14 each clamp has a fixed jaw 80 and a movable jaw 81 biased by a leaf spring 82 to closed position. The two bands 48 held by the fore and aft sets of clamps 56, 57 on the indexing chain 55 are also shown in FIG. 6.

Each movable jaw 81 is provided with a laterally extended cam follower arm 83 to open the clamp jaw 81 in opposition to the closing force of leaf spring 82 when the cam follower arm 83 contacts its cam rail 84 which is positioned just ahead of the stretched elastic band 48. Because there are two spaced bands 48 to pick up, each band 48 is acted upon by every other clamp 76. As shown in FIG. 6, the aft stretched band 48 is picked up by the jaws on clamp 76A and the fore elastic band 48 is picked up by the jaws on clamp 76B.

As best shown in FIG. 6, the clamped and stretched cut lengths 48 of elastic band are then carried around the arc at the end of chain 77 for application to the space 36 between discrete filler pads 32 on the film 40. This is shown along the bottom run of the longitudinally moving chain 77 in FIG. 6. The two bands 48 are laid down in the space 36 adjacent the notches 37 in the filler pads 32.

In FIG. 6 at the point reached by a clamp identified specially as clamp 76C, a cam rail 85 opens the movable clamp finger 81 on clamp 76C at the same time that an elastic band setting or pressing cam sector 86, which turns on the axis of its shaft 87, presses the stretched band 48 against the glue stripes 42 on film web 40 to adhere the stretched cut length of band 48 to the film web 40. Note in FIGS. 2 and 5 that the longitudinally moving chain 77 and its clamps 76 straddle the fabrication line 31 and are spaced beyond its edges so that the movable jaws 81 of the clamps 76 can open to their positions shown in FIG. 6, without interference with the fabrication line. At this point along the line, the tissue 51 and non-woven strips 53 are above the bands 48 so that the elastic band setting cam 86 will also press the cover strip 51 against the glue stripes 42.

After the bands 48 have been affixed to the film 40, as just explained, they are held in position as the web moves continuously through the machine by longitudinal band stretch maintaining clamps which are best shown in FIGS. 7 and 14. They are also shown schematically in FIGS. 1, 2 and 3 in which the clamps are mounted on longitudinally extending conveyor chains 90 which are above the web and similar longitudinal band stretch maintaining conveyors 91 which are below the web. The chains 90, 91 carry clamp bars 92, 93 which engage the bands 48 as they are released by the transfer clamps 76 as shown in FIGS. 7 and 14. Accordingly, transverse tension on the bands 48 is maintained by the clamps 92, 93 as the fabrication line 31 moves continuously forward and while the stripes of glue 42 set sufficiently to hold the elastic bands 48 in their stretched condition.

The clamps 92, 93 have footpads 94 to provide broad engagement with the stretched elastic bands 48. As the diapers move forward on the fabrication line, they will be contoured by a rotary contouring die 95 shown in FIGS. 1-3. After the longitudinal band stretch maintaining clamps 92, 93 release the bands 48, the successive shaped diapers in the fabrication line may be cut one from the other by final cut-off rotary knife 96 which works against an anvil roll 97, thus to form individual diapers 25, the side margins or thigh engaging margins of which are subject to the tension of the elastic bands 48. As soon as the diapers are released from between the clamps 92, 93, the tension of the bands 48 will pleat the diaper edges as shown near the right hand side of FIG. 2 and in FIG. 15. Take-away conveyor belt 98 (FIG. 3) is provided to move the pleated diapers 25 from the end of the fabrication line 31 for being grouped and packaged.

I claim:

1. A method of attaching elastic bands to flexible absorbent articles such as diapers comprising the steps of forming the articles in a continuous web comprising the articles which web extends longitudinally and is travelling longitudinally along a fabrication line and the length of the individual articles in the line is transverse to the longitudinally extending web, stretching elastic bands in a direction such that the longitudinal axes of the bands are transverse to the longitudinal travel direction of the web, attaching said bands to the web in their stretched condition and maintaining said bands in stretched condition transversely to the web until fabrication of the article in the web is completed and then allowing the bands to contract and pleat the article.

2. The method of claim 1 in which said elastic bands are cut to predetermined lengths after they are stretched and before applying them to the web.

3. The method of claim 2 in which said elastic bands are clamped to hold them in their stretched condition after they are cut and while being clamped applying them to the web for adherence to glue on the web and then clamping the applied bands to the web until the glue sets.

4. The method of claim 1 in which two elastic bands are concurrently stretched transversely of the longitudinal travel direction of the web, said bands being spaced longitudinally of the web a distance equal to the spacing between said bands in a single article.

5. The method of claim 1 plus the steps of indexing elastic bands into position transversely to the longitudinal travel direction of the web and picking said bands up from their indexed positions and transferring them in stretched condition to said articles at longitudinally spaced apart locations on the web.

6. The method of claim 5 plus the step of pressing said transferred bands against glue coated areas on the web and clamping said bands against said glue areas as the web moves longitudinally.

7. Apparatus for attaching elastic bands to a web composed of absorbent articles and comprising means for fabricating the web and in a continuous fabrication line in which a layer of pad material extends longitudinally along said fabrication line and the length of individual articles is transverse to the longitudinal direction of the web, means for stretching elastic bands in a direction such that the longitudinal axes of the bands are transverse to the longitudinal direction of the web, means for attaching said bands to the web in their stretched condition and for maintaining said bands in stretched condition transversely to the web until the articles composing the web are fabricated, and means for enabling the attached bands to contract to pleat the web.

8. The apparatus of claim 7 plus apparatus to cut the elastic bands to predetermined lengths after they are stretched and before the bands are applied to the web.

9. The apparatus of claim 8 in combination with means for clamping the elastic bands to hold them in their stretched cut length after cutting and means for transferring the bands while clamped to apply them to the web, means for gluing the bands to the web, and means for clamping the applied bands to the web until the glue sets.

10. The apparatus of claim 7 in which the apparatus for stretching the elastic bands comprises means for stretching two elastic bands concurrently with their longitudinal axes transverse to the longitudinal axis of the web and spaced from each other in the longitudinal direction of the web by a distance equal to the spacing of bands in a single article.

11. The apparatus of claim 7 in which the apparatus for stretching said bands includes means for indexing the bands from one position to another position transversely to the longitudinal direction of the web, in combination with means for picking said bands up from their indexed positions and transferring them in stretched condition to the web and in spaced relation along the longitudinal direction of the web.

12. The apparatus of claim 11 in combination with means for pressing the transferred bands against glue areas on the web and clamping said bands against said glue areas as the web moves in its longitudinal direction.

* * * * *